United States Patent [19]

Kapsokavathis et al.

[11] Patent Number: 5,231,358
[45] Date of Patent: Jul. 27, 1993

[54] CAPACITIVE FUEL COMPOSITION SENSOR WITH SLOW OSCILLATOR AND HIGH SPEED SWITCH

[75] Inventors: Nick S. Kapsokavathis, Shelby Township, Utica County, Mich.; Carl D. Wright, Noblesville, Ind.; Stephen P. Sanders, Millington, Mich.; Nick M. Johnson, Los Altos; Chun F. Cheah, San Francisco, both of Calif.

[73] Assignees: General Motors Corp., Detroit, Mich.; National Semiconductor Corp., Santa Clara, Calif.

[21] Appl. No.: 809,618

[22] Filed: Dec. 18, 1991

Related U.S. Application Data

[62] Division of Ser. No. 614,809, Nov. 16, 1990, Pat. No. 5,089,783.

[51] Int. Cl.⁵ .................... G01R 27/26; G01N 27/22
[52] U.S. Cl. .................... 324/672; 324/663; 324/690; 73/61.43; 307/351
[58] Field of Search .......... 324/605, 608, 658, 663, 324/664, 665, 672, 679, 688, 690; 73/61.41, 61.43, 116; 307/351, 354, 359; 328/115, 151

[56] References Cited

U.S. PATENT DOCUMENTS

| | | | |
|---|---|---|---|
| 3,639,779 | 2/1972 | Garrigus | 307/354 X |
| 3,816,811 | 6/1974 | Cmelik | 324/61 R |
| 4,001,676 | 1/1977 | Hile et al. | 324/60 CD |
| 4,438,749 | 3/1984 | Schwippert | 123/494 |
| 4,453,125 | 6/1984 | Kimura et al. | 324/58.5 A |
| 4,470,300 | 9/1984 | Kobayashi | 73/304 C |
| 4,471,295 | 9/1984 | Vermeiren | 324/672 X |
| 4,638,305 | 1/1987 | Sutton | 324/664 X |
| 4,706,630 | 11/1987 | Wineland et al. | 123/575 |
| 4,906,864 | 3/1990 | McCorkle | 307/356 X |
| 4,909,225 | 3/1990 | Gonze et al. | 123/494 |
| 4,915,084 | 4/1990 | Gonze | 123/575 |
| 4,939,467 | 7/1990 | Noglami et al. | 324/663 |
| 4,939,468 | 7/1990 | Takeuchi | 324/690 |
| 4,971,015 | 11/1990 | Gonze | 123/494 |

FOREIGN PATENT DOCUMENTS

1232675  5/1971  United Kingdom .

OTHER PUBLICATIONS

"Vehicle Operation with Variable Methanol/Gasoline Mixtures" VI Int'l Symposium on Alcohol Fuels Technology May 1984.
"An On-Board Sensor for Percent Alcohol" IEEE Transactions on Vehicular Technology, vol. VT-27, No. 3, Aug. 1978.
"Intelligent Alcohol Fuel Sensor", Schmitz et al, SAE Paper 900231, Society of Automotive Engineers, 1990.

Primary Examiner—Gerard R. Strecker
Assistant Examiner—Diep Do
Attorney, Agent, or Firm—Robert M. Sigler

[57] ABSTRACT

A fuel composition sensor provides to a voltage divider comprising sensor and reference capacitors a voltage which oscillates between two voltages at a comparatively low frequency, such as 6 KHz, for lower power dissipation, but which switches fast to produce periodic fast voltage changes across the voltage divider to produce voltage spikes at the junction of the capacitors indicative of the capacitance ratio and thus of fuel composition.

8 Claims, 4 Drawing Sheets

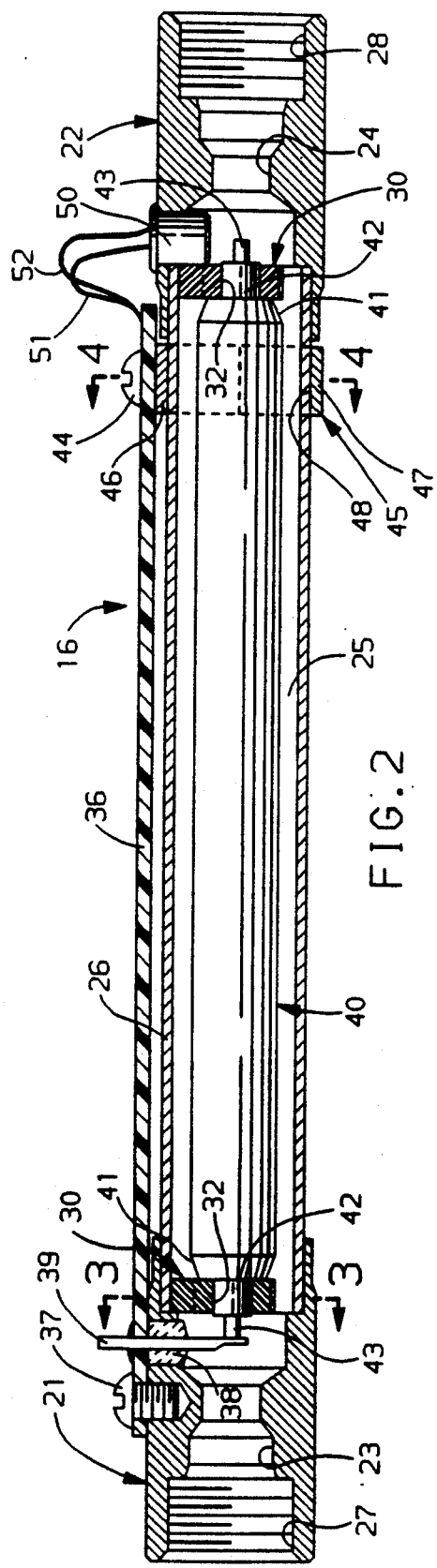
FIG. 2
FIG. 3
FIG. 4
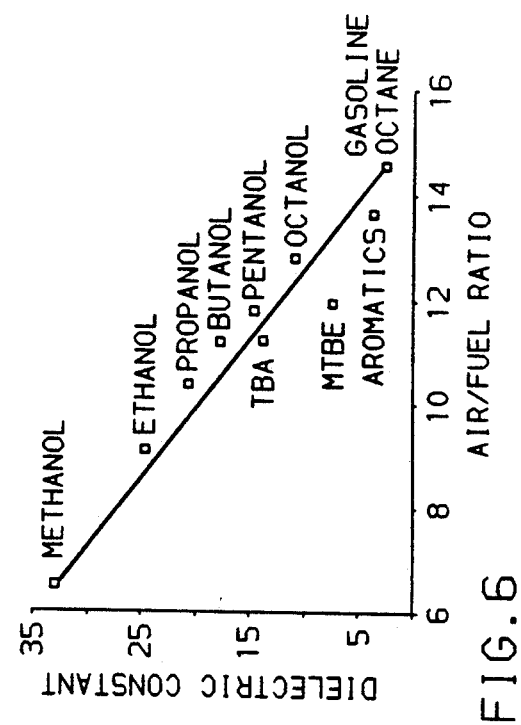
FIG. 6

CAPACITIVE FUEL COMPOSITION SENSOR WITH SLOW OSCILLATOR AND HIGH SPEED SWITCH

This application is a Division of U.S. Ser. No. 07/614,809, now U.S. Pat. No. 5,089,783, Capacitive Fuel Composition Sensor With Padding Capacitor, filed by Nick S. Kapsokavathis and Stephen P. Sanders on Nov. 16, 1990 and assigned to an assignee of this application.

BACKGROUND OF THE INVENTION

This invention relates to combustion engine driven vehicles and particularly to such vehicles adapted to operate on a mixture of fuels such as gasoline and alcohol in unknown, variable concentrations. The engines of such vehicles are optimally operated with one or more engine operating parameters varied in response to a fuel composition signal generated by a sensor in the engine fuel supply which is responsive to a parameter of the fuel mixture indicating fuel composition.

Several types of fuel composition sensors for vehicle engines are known in the prior art. These include optical, microwave and capacitive sensors. In the field of capacitive fuel composition sensors, a problem which must be overcome is the electrical conductivity of alcohols, which tends to greatly decrease accuracy of the sensors at alcohol concentrations greater than 30 percent, due to the short circuiting of the capacitor plates through the fuel mixture.

U.S. Pat. No. 4,915,084, Combustion Engine with Multi-Fuel Capability, issued Apr. 10, 1989 to Eugene V. Gonze and assigned to an assignee of this application, describes a capacitive fuel composition sensor capable of operating accurately at alcohol concentrations up to 100 percent. This sensor provides a capacitor in the engine fuel line, an electrical reference impedance in series combination with the capacitor, and an oscillator providing an oscillating voltage to the capacitor/impedance combination with a voltage component having a frequency of at least 1 Megahertz but less than a frequency requiring microwave circuit apparatus. The sensor further includes an electric circuit responsive to a capacitively determined electrical parameter of the capacitor to determine the capacitance thereof and therefore the dielectric constant of the fuel mixture. The high frequency of the voltage component used for capacitance sensing provides a capacitor impedance significantly lower than the parallel equivalent resistive impedance of the fuel due to fuel conductivity, so that the capacitive impedance predominates and the sensor thus provides an accurate indication of capacitance.

SUMMARY OF THE INVENTION

The sensor of this invention provides to a voltage divider comprising sensor and reference capacitors a voltage which oscillates between two voltages at a comparatively low frequency, such as 6 KHz, for lower power dissipation, but which switches fast to produce periodic fast voltage changes across the voltage divider to produce voltage spikes at the junction of the capacitors indicative of the capacitance ratio and thus of fuel composition.

Further details and advantages of this invention will be apparent from the accompanying drawings and following description of a preferred embodiment.

SUMMARY OF THE DRAWINGS

FIGS. 2-4 are various views as indicated of a sensing capacitor for use in the fuel composition sensor according to the invention.

FIG. 6 shows a graph of dielectric constant vs. required air/fuel (A/F) ratio for combustion for a variety of fuels.

DESCRIPTION OF THE PREFERRED EMBODIMENT

Figure 1:
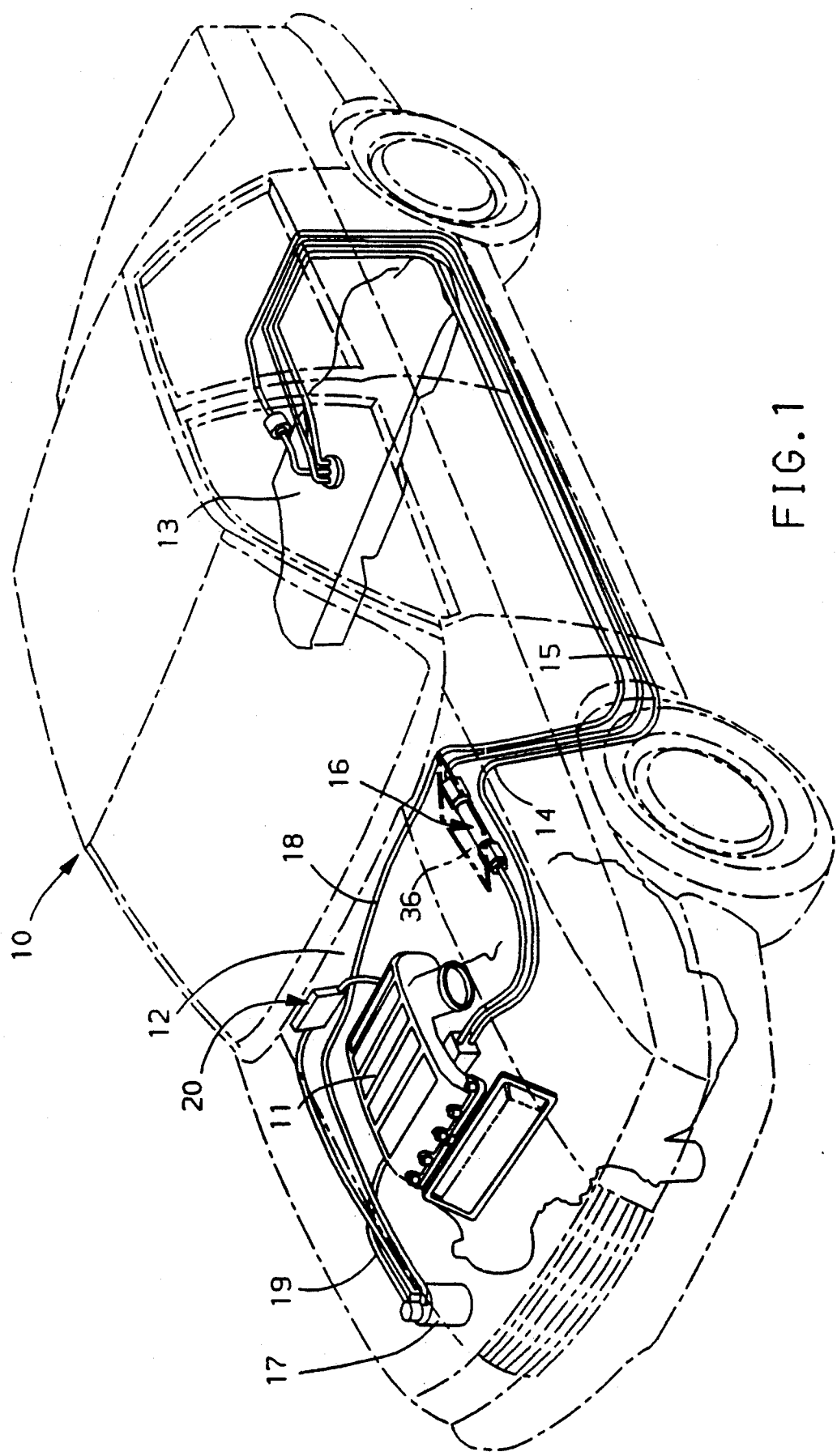
FIG. 1 shows a motor vehicle having an engine fuel control with a fuel composition sensor according to this invention.

Referring to FIG. 1, a motor vehicle 10 is provided with an internal combustion engine 11 in an engine compartment 12, engine 11 receiving fuel from a fuel tank 13 at the opposite end of the vehicle through a fuel conduit 15 and returning excess fuel to tank 13 through fuel conduit 14. The fuel in tank 13 is a mixture of essentially two fuels, one of which is gasoline and the other of which is an alcohol such as methanol or ethanol. Fuel conduit 15 includes a fuel composition sensor 16 located within engine compartment 12 at a point close to engine 11. Fuel composition sensor 16 generates a signal indicative of the relative proportion of alcohol to gasoline in the fuel flowing therethrough. A standard fuel vapor collection canister 17 is connected by a vapor conduit 18 to fuel tank 13 for collection of vapor therefrom and another vapor conduit 19 to the induction system of engine 11.

The operation of engine 11 is controlled by an electronic controller 20, which may be located at the rear of the engine compartment as shown or any other convenient location. Controller 20 may be a programmed digital computer similar to those presently used in motor vehicles for engine control. The apparatus is well known, comprising a microprocessor, RAM, ROM and appropriate input/output circuitry, with an appropriate program stored in ROM to coordinate receipt of input information from various sensors, perform calculations and table look-ups and output commands to various actuators of engine related components. Controller 20 is responsive to the fuel composition signal VOUT from fuel composition sensor 16 as well as a fuel temperature signal therefrom to modify such engine operating parameters as the air/fuel ratio, ignition timing, canister purge rate and/or others as necessary to optimize engine operation for the actual fuel mixture provided to the engine as sensed by sensor 16.

The mechanical structure of sensor 16 is shown in FIGS. 2-4. This structure provides for a common ground between the sensor case and the outer capacitor electrode, so that it is not necessary for these parts to be insulated from each other. The cost savings due to the grounded outer electrode are greater than the cost of any additional electronics required in the sensor due to this design feature.

An outer tube 26 of low carbon stainless steel has one end fitted within and laser welded to an extended open end of a coupling member 21 and another end fitted within and laser welded to an extended open end of another coupling member 22. Coupling members 21 and 22 are both made of stainless steel, have an outer hexagonal shape and define passages 23 and 24, respectively, therethrough, each of which passages 23 and 24 is provided with an internally threaded portion 27 and 28, respectively, for attachment in fuel line 15. Outer tube 26 forms a portion of the outer case of the sensor as well as the outer electrode of a sensor capacitor.

A stainless steel inner tube 40 is disposed axially within outer tube 26 to form the inner electrode of the sensor capacitor and to define an annular chamber 25 between tubes 26 and 40. Inner tube 40 is closed at each end in a tapered portion 41, a smaller diameter cylindrical portion 42 and an extended axial nipple 43, all made of stainless steel. Inner tube 40 is suspended at each end thereof within outer tube 26 by spacers 30, seen axially in FIG. 3. Each spacer 30 includes an inner portion 31 having a circular opening 32 which receives cylindrical portion 42 of inner tube 40 and three radially projecting legs 33 at 120 degree angles with respect to each other which end at outer tube 26, the legs 33 defining openings 34 therebetween. Spacers 30 may be made of an alcohol resistant, electrically insulating polymeric resin such as Nylon (R). A fuel flow path is thus defined through passage 24 of coupling member 22, through openings 34 between the legs 33 of a spacer 30, through annular chamber 25 between tubes 26 and 40, through openings 34 between the legs 33 of the other spacer 30, and through passage 23 of coupling member 21. The fuel in chamber 25 between tubes 26 and 40 forms the dielectric of the sensor capacitor defined by these electrodes.

A circuit board 36, of standard four layer (signal, power, ground, signal) construction, is attached to coupling member 21 by a machine screw 37, which not only physically anchors one end of board 36 but also provides a ground connection between a ground circuit trace on circuit board 36 and, through coupling member 21, tube 26, which thus comprises a grounded electrode of the sensor capacitor. Between screw 37 and the adjacent spacer 30, a glass insulator 38 is retained in an opening of coupling member 21 adjacent circuit board 36. A stainless steel pin 39 projects through circuit board 36 and insulator 38 so that it does not contact coupling member 21 or tube 26. Pin 39 is maintained in physical and electrical contact, as by welding or soldering, to the adjacent nipple 43 and is soldered on circuit board 36 to the appropriate circuit trace for the inner electrode of the sensor capacitor. The total distance between the connections of pin 39 to circuit board 36 and to nipple 43 is 9.7 mm. Thus, both the inner and outer electrodes of the sensor capacitor are electrically coupled to the circuit board through a minimal length of conductor.

The opposite end of circuit board 36 is attached by a pair of screws 44 to a clamp 45 comprising upper and lower clamp members 46, 47, respectively. Screws 44 hold clamp members 46 and 47 together as well as securing clamp 45 to circuit board 36. Clamp members 46 and 47 include matching semicircular openings which, together, define an inner circular opening 48 for receiving outer tube 26. Clamp 45 fits snugly around tube 26 to hold the opposite end of circuit board 36 in a stable manner without undue vibration relative to tube 26 but allows relative rotation so that twisting torques applied between coupling members 21 and 22 are not applied to circuit board 26. In practice, to protect the components of circuit board 36 and other parts of the sensor from the environment, a supplemental external case, not shown, may be attached to sensor 16 as by a machine screw in a threaded depression, not shown, opposite screw 37 and at clamp 45, for example by extending bolts 44 completely therethrough, to surround all of the sensor except the hexagonal ends of couplings 21 and 22.

A fuel temperature sensor 50 is received in a sealing manner in the wall of coupling member 22 so as to be exposed to fuel within and generate a fuel temperature signal communicated to an appropriate circuit trace(s) on circuit board 36 through wire leads 51 and 52. Fuel temperature sensor 50 may be a thermistor or any other type of temperature sensor appropriate for sensing the temperature of fluids and provides a necessary temperature correction signal for the sensor output. The fuel temperature signal may be separately output to engine control computer 20 for temperature compensation of the fuel composition signal VOUT.

Although all openings and gaps within the sensor are of sufficient size to prevent them from presenting a significant restriction to fuel flow, the total volume of fuel contained within chamber 25 is minimized with out of flow volumes eliminated or reduced to prevent extreme flow rate reduction or accumulation of fuel within chamber 25 which might lead to differences in dielectric constant between the fuel mixture in the sensor and that about to enter the combustion chamber of engine 11.

Figure 5:
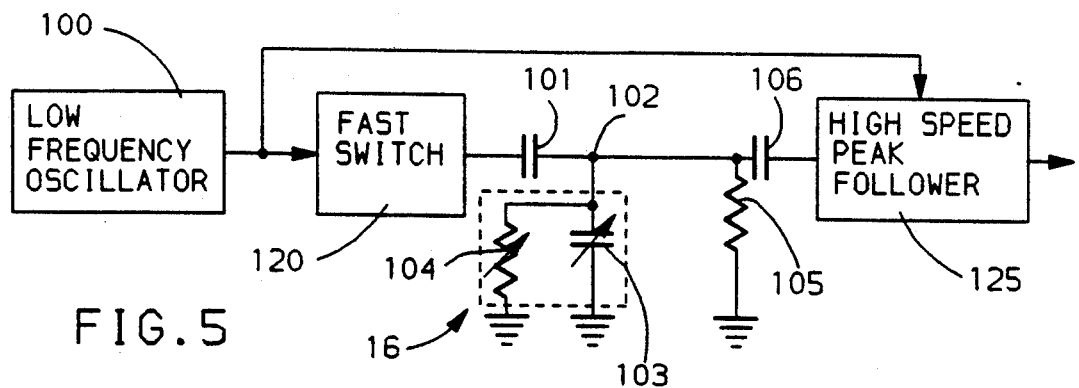
FIG. 5 shows a block and circuit diagram of a portion of a fuel composition sensor according to the invention.

The sensor electronics are shown in FIG. 5. These components are mounted on circuit board 36 in the sensor package. In an integrated circuit (IC) version of the circuit, as many of them as possible would be included in an IC that would be one of the circuit board components. The components are provided with a regulated voltage V+ of, for example, 6.5 volts and, through an input isolation amplifier to be described, a smaller regulated voltage VREF of 5.0 volts, both with reference to a sensor ground voltage terminal of the circuit board 36 and thereby tube 26 of the sensor capacitor defining a sensor ground voltage GND. The standard voltage regulator circuit for producing voltage V+ is not shown.

Referring to FIG. 5, a low frequency oscillator 100 generates an output voltage which varies between V+ and ground at a comparatively low frequency such as 6 KHz. This output voltage is adapted to control the conductive state of a fast switch 120, which alternately connects VREF and ground to one end of a reference capacitor 101, (680 pF) connected through sensor 16 to ground. Reference capacitor 101 and sensor 16 define a junction 102 therebetween so as to form a voltage divider with an output at junction 102. Sensor 16 comprises a sensor capacitor 103 having coaxial electrodes comprising tubes 26 and 40 of FIGS. 2-4 with a fuel mixture dielectric in chamber 25 therebetween as previously described and further comprises a parallel leakage resistance 104 through the fuel mixture in chamber 25. The capacitance of sensor capacitor 103 varies with the dielectric constant of the fuel mixture between its electrodes (e.g. 39–755 pF for gasoline and methanol); and leakage resistance 104 varies with the electrical conductivity of the same fuel mixture. Thus, each varies with fuel composition. A bias resistor 105 (10K) is also provided between junction 102 and ground to provide a steady state ground bias at junction 102. A high speed peak detector 125 has a signal input connected through a DC blocking capacitor 106 (0.22uF) to junction 102 and a latch input receiving the output of oscillator 100. In addition, there is a stray capacitance of 6–10 pF from junction 102 to ground.

Figure 8:
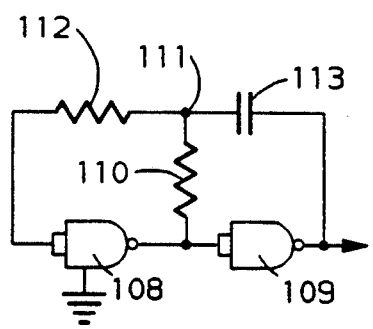
FIGS. 8-10 show diagrams of circuits for use as a low frequency oscillator, fast switch and high speed peak follower, respectively, in the fuel composition sensor of FIG. 5.

Low frequency oscillator 100 may be any convenient oscillator circuit capable of operating at a frequency at or near 6 KHz. An example is the relaxation oscillator of FIG. 8, utilizing series NAND gates 108 and 109 connected as series inverters. The output of inverter (NAND gate) 109 is connected back through a capacitor 113 (0.0047 uF) and resistor 110 (15K) in series to its input with the junction 111 of capacitor 113 and resistor 110 being connected through a resistor 112 (100K) to the input of inverter (NAND gate) 108, the output of which is connected to the input of inverter (NAND gate) 109.. The component values are chosen to produce an oscillator output voltage which switches between the oscillator supply voltages (V+ and ground) at the desired 6 KHz frequency, as shown in waveform 180 of FIG. 7(A). This oscillator is a standard CMOS circuit well known to those skilled in the art and suitable for component assembly on a circuit board. In an IC version, this circuit would be replaced by another in the appropriate IC technology.

Figure 9:
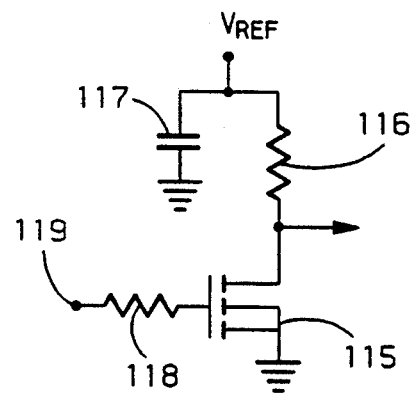

An example of fast switch 120 is shown in FIG. 9. A fast switching MOSFET 115, such as the Motorola (R) 2N7000 or its equivalent, is chosen to obtain a switching speed of 30 nanoseconds. Actually, the switching speed of the device with no added gate resistance is 10–15 nanoseconds; and a 510 ohm resistor 118 is placed in series with the gate to form a small RC delay with the internal gate capacitance and thus slow the switching speed down to the optimum 30 nanoseconds. MOSFET 115 has a grounded source and a drain connected through a resistor 116 (10K) to VREF, which is provided with a bypass capacitor 117 (0.22 uF) to ground to keep switching noise out of the power supply. The drain of MOSFET 115 is the output of fast switch 120, which output is connected to reference capacitor 101.

In operation, oscillator 100 causes MOSFET 115 to be turned on and off at a frequency of 6 KHz. The voltage at the drain of MOSFET 115 is shown in waveform 182 of FIG. 7(B) and approaches a 6 KHZ square wave. However, it is not a perfect square wave, since the voltage transitions are not instantaneous. The ramps of the voltage transitions are exaggerated for visibility in FIG. 7(B). Just before MOSFET 115 is turned on, the voltage on its drain is at VREF. Reference capacitor 101 is charged to VREF, with junction 102 at ground. As MOSFET 115 turns on, its drain voltage goes to ground in 30 nanoseconds. If there were no resistive current path to ground from junction 102, its voltage would drop, in the same time, to a voltage dependent on the capacitive voltage divider ratio as described above and thus on the fuel composition. The 10K resistance of resistor 105 does not allow sufficient leakage current to significantly affect the fast voltage drop at junction 102; however, it allows the capacitors to discharge after the immediate voltage drop so that the voltage on junction 102 returns to ground.

However, leakage resistance 104 will be much smaller than the 10K of resistor 105 at high methanol concentrations (above 30 percent methanol, for example) and will allow a significant portion of the capacitor charge to leak away before MOSFET 115 turns completely on unless the switching of fast switch 120 is extremely fast. Such a loss of charge would result in the voltage at junction 102 not dropping as far before rising again; and the abbreviated voltage peak would create an error in the indicated fuel composition. The faster the switching of fast switch 120, up to a point, the less charge will be lost and the more accurate will be the downward voltage spike at junction 102 in indicating the fuel composition. A single bipolar transistor, with a typical switching time of 70–100 nanoseconds, is not fast enough. A network of bipolar transistors can be constructed with a faster switching time, at the price of additional cost and circuit complexity. MOSFET 115, as previously mentioned, has a switching time (in turning on) of 10–15 nanoseconds; but this is too fast, due to the inductance of the leads (pin 48 and the combination of coupling 21 and screw 37) of sensor capacitor 103 between electrode members 26 and 40 and the circuit board. This inductance causes inaccuracies at very fast switching speeds. For example, the inductance can produce a ringing which causes a delay in the downward voltage spike at junction 102 while energy is temporarily stored in the inductive fields of the leads. More charge can leak off the capacitors during this ringing. Also, the inductance of the leads produces a voltage drop along the leads of about 50 millivolts for each ¼ inch of lead - at each end of the capacitor. Each of these factors contributes to the inaccuracy of the sensor; and this inaccuracy tends to increase with the speed of switching. It has been determined that a 30 nanosecond switching time provides the optimum signal with the lowest error at high methanol concentrations. Lower switching speeds allow more charge to leak off for a more abbreviated output voltage peak. However, faster switching speeds increase error due to the inherent inductances of the sensor capacitor leads.

There are additional considerations of importance in the design of the circuit described to this point. Resistor 116 is given a value of 10K. This value is chosen as a compromise between competing factors. It is desired that, when MOSFET 115 is on or conducting, the voltage at its drain be essentially ground. Actually, its drain voltage will be determined by the voltage divider effect of resistor 116 over the internal drain/source impedance of MOSFET 115, which is a few ohms. The larger the resistance of resistor 116, the closer the drain voltage will be to ground during MOSFET conduction. However, it is also necessary that reference capacitor 101 be recharged to a full VREF during each oscillator cycle prior to the turning on of MOSFET 115. Since resistor 116 is in the charging path of reference capacitor 101, an increase in its resistance means a longer charging time; and 20K produces too long a time for the other component values used. The oscillator frequency is likewise a compromise between competing factors. A lower frequency will increase the size of an integrator capacitor 150 yet to be described; and this will slow the overall response time. However, a higher frequency would allow even less time for the recharging of reference capacitor 101 during each oscillator cycle and put additional downward pressure on the resistance of resistor 116 as described above.

Figure 7:
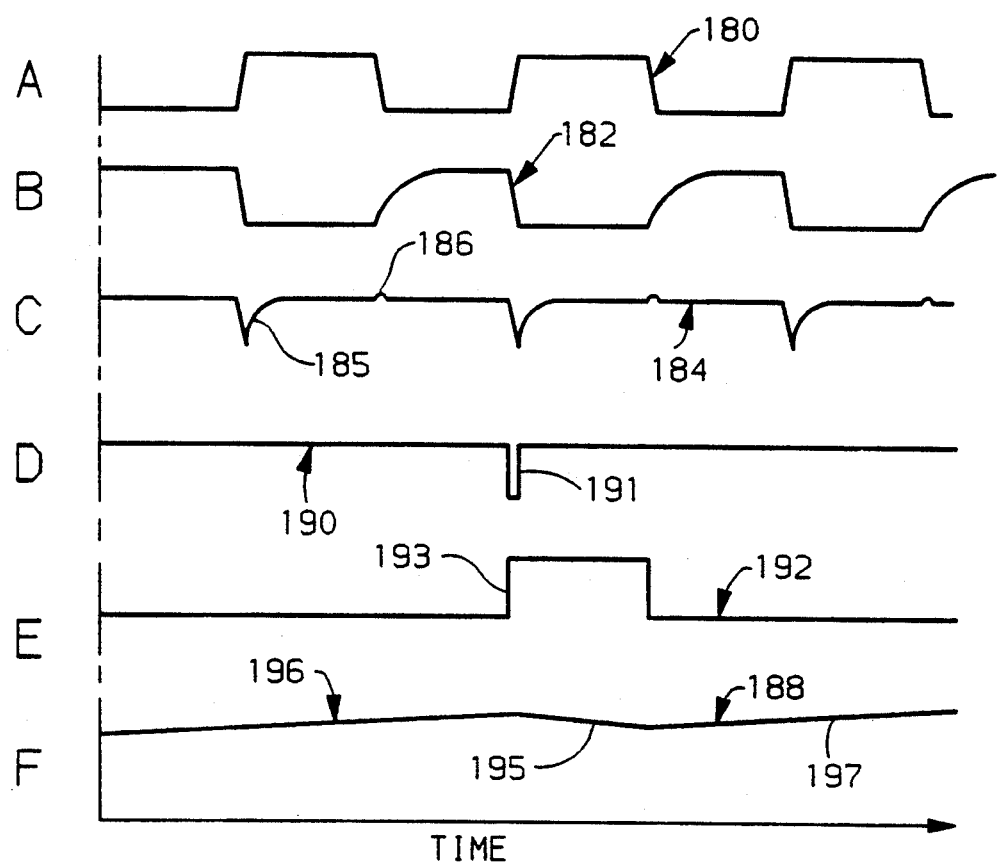
FIG. 7 shows a series of voltage waveforms useful in understanding the operation of the circuit of FIG. 5.

The voltage waveform at junction 102 is seen in waveform 184 of FIG. 7(C). Each downward spike 185 is a new capacitance (and therefore fuel composition) measurement. The smaller upward spikes 186 are due to the same effect in the opposite direction during the alternate oscillator phases as MOSFET 115 is turned off. These upward spikes are ignored in the following circuitry. The voltage at junction 102 is upward shifted and peak detected by the following high speed peak detector 125 to provide an analog output signal between ground and VREF.

Figure 10:
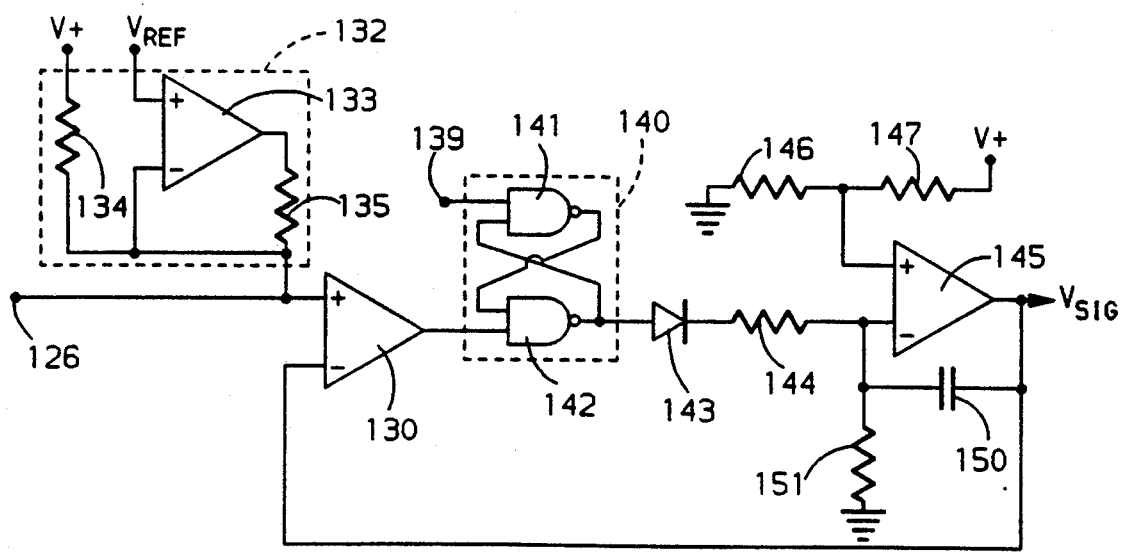

An embodiment of high speed peak detector 125 is shown in FIG. 10. Input terminal 126 from capacitor 106 is connected to a pull-up circuit 132 which comprises an op-amp 133 (LM158) having a non-inverting input connected to VREF, an inverting input connected through a resistor 134 to V+ and an output connected through a resistor 135 (10K) to terminal 126 and to its inverting input. This circuit shifts the voltage at junction 102 upward by VREF to get it above ground for the following circuitry, with DC blocking capacitor 106 of FIG. 5 separating the different voltage level portions of the circuit.

Terminal 126 is also connected to the non-inverting input of a fast comparator 130 (LT1016), the output of which is provided to one input of a NAND gate latch 140 comprising NAND gates 141 and 142 and having another input 139 connected to the output of low frequency oscillator 100. The output of latch 140 is provided through a diode 143 and resistor 144 (100K) to the inverting input of an op-amp 145 (LM158) having a non-inverting input provided with a constant reference voltage from a voltage divider comprising resistors 146 and 147 in series across voltage V+. The output of op-amp 145 is fed back to the inverting input through a capacitor 150 (0.33 uF) and is further provided as the output of the sensor and as a reference to the inverting input of fast comparator 130. The inverting input of op-amp 145 is connected through a resistor 151 (750K) to ground. Fast comparator 130 requires a higher DC bias current than normal slower comparators, which is provided by circuit 132. Circuit 132 has a high impedance during the downward spikes 185 of FIG. 7(C) so as to reduce sensor inaccuracy due to this high DC bias current.

The operation of the remainder of the circuit of FIG. 10 will be described with relation to the waveforms of FIGS. 7(D)–7(F). Sensor voltage VSIG, determined by an integrator comprising op-amp 145 and its feedback capacitor 150, is shown as waveform 188 of FIG. 7(F). During each half oscillator cycle in which the oscillator output is low, the latch output of NAND gate 142 is held low and capacitor 150 is allowed to discharge through resistor 151. The comparatively high value of resistor 151 assures a slow discharge for a slowly rising VSIG. During the opposite half cycle of oscillator 100, in which the oscillator output is high, the latch output remains low unless the high speed comparator output goes low, which will occur if the downward spike of the voltage at junction 102, shifted upward by circuit 132, falls below the sensor voltage VSIG. The output of fast comparator 130 is shown as waveform 190 of FIG. 7(D); and one such downward spike 191 is shown. The response of latch 140 is to switch its output, shown as waveform 192 of FIG. 7(E), high for the remainder of the oscillator half cycle, as shown at 193. Capacitor 150 will charge through diode 143 and resistor 144, at a significantly faster rate than the discharge due to the smaller value of resistor 144; and sensor voltage VSIG will thus fall comparatively rapidly, as shown in portion 195 of waveform 188. The usual constant slow rise of VSIG, as shown in portions 196 and 197 of waveform 188, is punctuated by briefer, faster falls, as shown in portion 195, as VSIG follows the downward peaks of the voltage at junction 102 to maintain a level indicating the capacitance of sensor capacitor 103 and therefore of fuel composition.

The voltage VREF-GND is applied across resistor 116 and switching MOSFET 115 of FIG. 9 in the sensor circuit of FIG. 5. VREF is also provided to the pull-up circuit 140 described with reference to FIG. 10. The equivalent equation for the sensor circuit of FIGS. 5, 8, 9 and 10 is $$VSIG - GND = (VREF - GND)(1 - CAPRATIO).$$

CAPRATIO is the capacitance ratio $C_{101}/(C_{101} + C_{103} + C_{stray})$, wherein $C_{101}$ and $C_{103}$ are the capacitances of reference capacitor 101 and sensor capacitor 103 and $C_{stray}$ is the stray capacitance of the sensor.

The embodiments of the invention in which an exclusive property of privilege is claimed are defined as follows:

1. A fuel composition sensor for a fuel mixture in a fuel supply line for a combustion engine wherein the fuel mixture comprises two fuels of different dielectric constants in unknown relative concentrations, at least one of the fuels being electrically conductive, the sensor comprising, in combination:
  a sensor capacitor in the fuel line adapted for fuel flow therethrough so that the fuel mixture provided to the engine comprises a dielectric which determines the capacitance thereof but also comprises a capacitor shorting electrical conductance;
  a reference capacitor of constant capacitance in series with the sensor capacitor to form therewith a voltage divider having an output junction; and
  circuit means comprising a square wave oscillator with an output high speed switching MOSFET connected in series with a resistance across an electric power supply, the reference and coupling capacitors being connected in series across the MOSFET with the coupling capacitor having an electrode connected to the junction of the resistance and MOSFET, the circuit means being effective to repetitively produce, at a comparatively low frequency, a predetermined fast voltage change across the series combination of the reference and sensor capacitors to produce a corresponding voltage change at the output junction comprising an initial voltage change essentially proportional to the capacitance ratio of the sensor and reference capacitors followed by an opposite voltage change due to leakage current through the fuel mixture, whereby the initial voltage change indicates the fuel composition.

2. The fuel composition sensor of claim 1 in which the MOSFET has a conduction initiation time less than 30 nanoseconds and a conduction controlling gate to alternately initiate and stop MOSFET conduction at the low frequency to produce the fast voltage change alternately with the opposite voltage change, the gate of the MOSFET having a series connected resistor forming an RC delay with an inherent capacitance of the MOSFET to slow the conduction initiation time to 30 nanoseconds.

3. A fuel composition sensor for a fuel mixture in a fuel supply line for a combustion engine wherein the fuel mixture comprises two fuels of different dielectric constants in unknown relative concentrations, at least one of the fuels being electrically conductive, the sensor comprising, in combination:

a sensor capacitor in the fuel line adapted for fuel flow therethrough so that the fuel mixture provided to the engine comprises a dielectric which determines the capacitance thereof but also comprises a capacitor shorting electrical conductance;

a reference capacitor of constant capacitance in series with the sensor capacitor to form therewith a voltage divider having an output junction;

circuit means for repetitively producing, at a comparatively low frequency, a predetermined fast voltage change across the series combination of the reference and sensor capacitors to produce a corresponding voltage change at the output junction comprising an initial voltage change essentially proportional to the capacitance ratio of the sensor and reference capacitors and defining a peak sensor voltage which indicates the fuel composition, followed by an opposite voltage change due to leakage current through the fuel mixture, whereby the initial voltage change indicates the fuel composition; and a peak detector circuit coupled to the output junction to provide a continuous signal of fuel composition from successive peak sensor voltages.

4. The fuel composition sensor of claim 3 in which the fast voltage change has a time duration of substantially 30 nanoseconds.

5. The fuel composition sensor of claim 3 in which the low frequency is not substantially greater than 6 Kilohertz.

6. The fuel composition sensor of claim 3 in which the peak detector circuit comprises:

signal difference means having a first input coupled to the output junction, a second input and an output providing the difference thereof;

a latch having first and second states, the latch being responsive to the circuit means and signal difference means for maintaining the first state during first periods and maintaining the second state during second periods alternating with the first periods and occurring when the peak sensor voltage exceeds the voltage at the second input of the signal difference means;

an integrator capacitor providing a voltage to the second input of the signal difference means; and capacitor charging means responsive to the latch to charge the integrator capacitor in a first direction at a first rate with the latch in its first state and to charge the integrator capacitor in a second direction at a faster second rate with the latch in its second state.

7. The fuel composition sensor of claim 6 further comprising a DC isolation capacitor between the output junction and the first input of the signal difference means and a voltage level shifting circuit connected to the first input of the signal difference means.

8. The fuel composition sensor of claim 3 in which the circuit means comprises a square wave oscillator with an output high speed switching MOSFET connected in series with a resistance across an electric power supply and the reference and coupling capacitors are connected in series across the MOSFET with the coupling capacitor having an electrode connected to the junction of the resistance and MOSFET.

* * * * *